United States Patent
Ritzoulis et al.

(10) Patent No.: US 9,579,618 B2
(45) Date of Patent: Feb. 28, 2017

(54) EMULSIFIERS FROM GRAPE PROCESSING BY-PRODUCTS

(71) Applicants: Christos Ritzoulis, Thessaloniki (GR); Alexandros Pavlou, Thessaloniki (GR); Costas Panayiotou, Thessaloniki (GR)

(72) Inventors: Christos Ritzoulis, Thessaloniki (GR); Alexandros Pavlou, Thessaloniki (GR); Costas Panayiotou, Thessaloniki (GR)

( * ) Notice: Subject to any disclaimer, the term of this patent is extended or adjusted under 35 U.S.C. 154(b) by 0 days.

(21) Appl. No.: 14/741,467

(22) Filed: Jun. 17, 2015

(65) Prior Publication Data

US 2016/0367958 A1    Dec. 22, 2016

(51) Int. Cl.
*B01F 17/00* (2006.01)
*C11B 3/00* (2006.01)
*A61K 36/87* (2006.01)

(52) U.S. Cl.
CPC ........ *B01F 17/0092* (2013.01); *B01F 17/005* (2013.01); *B01F 17/0028* (2013.01); *A23V 2250/21* (2013.01); *A61K 36/87* (2013.01); *A61K 2236/37* (2013.01); *C11B 3/006* (2013.01)

(58) Field of Classification Search
CPC ............... A61K 36/87; A61K 2236/37; A23V 2250/21; C11B 3/006
See application file for complete search history.

(56) References Cited

U.S. PATENT DOCUMENTS

| | | | |
|---|---|---|---|
| 4,265,925 A | 5/1981 | Campbell | |
| 6,238,673 B1 | 5/2001 | Howard | |
| 6,544,581 B1 * | 4/2003 | Shrikhande | ........... A23L 1/2751 426/425 |
| 8,252,347 B1 | 8/2012 | D'Amelio | |
| 8,512,771 B2 | 8/2013 | Ianiro | |
| 2005/0129790 A1 * | 6/2005 | Folts | ..................... A23L 1/3002 424/766 |
| 2007/0122505 A1 | 5/2007 | Elgaard | |

FOREIGN PATENT DOCUMENTS

| | | |
|---|---|---|
| WO | 0072953 A2 | 12/2000 |
| WO | 2006111163 A1 | 10/2006 |
| WO | 2009019088 A1 | 2/2009 |
| WO | 2010070836 A1 | 6/2010 |
| WO | 2014018922 A1 | 1/2014 |

OTHER PUBLICATIONS

Interview Agenda from Cristos Ritzoulis received Aug. 7, 2016.*
PTOL-413A Interview Request form from Cristos Ritzoulis received Aug. 7, 2016.*
Pavlou A., Panayiotou C., Ritzoulis C., Filotheou A. Hydrocolloids From Grape Pomaces 10th Pan-Hellenic Conference of Chemical Engineering, Jun. 4-6, 2015, Patras, Greece.

* cited by examiner

*Primary Examiner* — Michael A Salvitti

(57) ABSTRACT

A process is described by which the solid waste of grape resulting from processes such as vinification, is treated with hot steam, then is treated with alcoholic solutions, the alcohol being removed, then the oil residues present in the solid residue are removed. The said solid residue is then subjected to aqueous extractions, the aqueous medium is separated from the remaining solids, and this aqueous medium is concentrated. The said material is also described, being capable of emulsifying oil-in-water emulsions and provide stability to colloids.

9 Claims, 1 Drawing Sheet

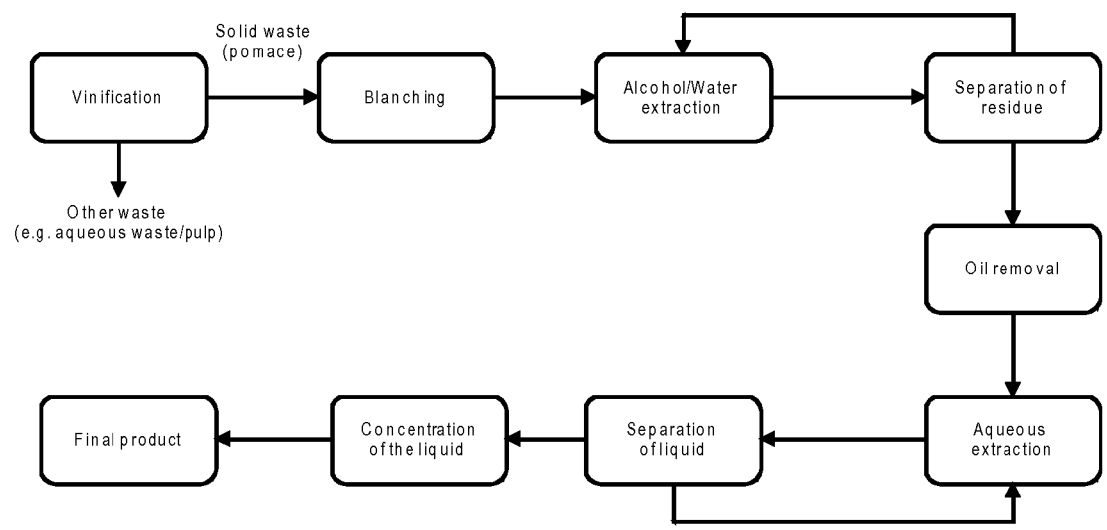

EMULSIFIERS FROM GRAPE PROCESSING BY-PRODUCTS

CROSS REFERENCE TO RELATED APPLICATIONS

Patent U.S. Pat. No. 8,512,771 B2 "Method of preparing a muscadine pomace extract" describes a method of producing a muscadine pomace extract, as it is extracted from the juice of the fruit. The method includes combination of a bronze muscadine pomace extract with a purple muscadine pomace extract, as to produce a muscadine pomace extract. Muscadine belongs to the specie *rotundifolia* of the genus *vitis*, and the end product of the method, aims to be used mainly as an antioxidant and can contain additional substances that are customarily used in cosmetics as emulsifiers or thickeners. The process of isolation and the composition of the final product are different than the ones described in the present Invention.

U.S. Pat. No. 6,544,581 B1 patent claims rights to a process for extraction, purification and concentration of polyphenol substances from whole grapes, grape seeds and grape pomace. The liquid and powdered products of the present processes are particularly rich in polyphenolics, including anthocyanins, catechin monomers and their oligomers, which are not related to the reclaim of emulsifiers, which are the subject materials of the present patent.

U.S. Pat. No. 8,252,347 B1 patent claims rights to a stabilizing and antioxidant composition prepared from the residue obtained from the saw palmetto berry. Saw palmetto berry is the fruit of the plant *Serenoa repens*. The residue from the saw palmetto berry exhibits antioxidant properties that can be used to stabilize various compositions such as food or edible compositions and cosmetics.

WO 2014018922 A1 claims rights to a protein isolate from soy processing by-products. The said invention is concerned with aqueous whey streams in the soy industry and the soy whey proteins isolated with emulsifying capabilities. The above invention is related to soy processing waste products, while the present invention pertains to grape processing waste, which is an entirely different material.

WO 2006111163 A1 patent describes a method for producing plant extracts through incubation of a plant material with an enzyme composition comprising a lipolytic enzyme. It is based on the contact of the plant material with a lipolytic enzyme, rather than its aqueous extraction which is the focus of the present Invention.

In the WO 2010070836 A1 patent rights are claimed on a grape pericarp extract which is rich in 3-mercaptohexan-1-ol precursors. The end product is extracted at relatively low temperatures (30-60) to prevent decomposition of the 3-mercapto-hexane-1-ol precursors, and it can be used in the production of a soft drink, as it is described in this patent. Therefore, the material of the patent in question is not related to the reclaim of emulsifiers or similar materials.

In U.S. Pat. No. 4,265,925 patent a method is described, in order to purify plant proteins from mixtures with carbohydrates and flavors. This method involves utilization of fluidized bed, inert gas treatment and an overall technology different from the one proposed herein. The end product of the invention is protein concentrate to be used as protein replacer in meat products, rather than emulsifying or stabilizing agents for other applications. The process as a whole is different from the one described in this Invention.

Patent U.S. Pat. No. 6,238,673 B1 "Method of producing high flavonol content polyphenol compositions" describes a method of producing a polyphenol-containing composition derived from grapes or grape pomace. The end product is different than the subject materials of the present Invention, while they are not intended to be used as emulsifiers.

In the WO 2009019088 A1 patent rights are claimed to a natural stabilizer system that can be used in frozen desserts. The material of this patent comprise native rice starch, egg yolk as a natural emulsifier and fibres from vegetables, fruits or mixtures thereof. The acquisition of this material does not include the extraction of Alcohol Insoluble Solids, while the overall process of extraction is different from the one described in the present Invention.

Patent WO 2000072953 A2 "A method of producing organic emulsifiers and organic surfactants, products produced by said method, and the use of such products" describes a method for producing organic emulsifiers and organic surfactants and to the organic emulsifiers and organic surfactants produced by said method, from organically produced sources, e.g. organically produced plants. However, this production is based on the oil or fat from these organically produced sources, which are removed during the process described in the present Invention.

Patent US 20070122505 A1 involves the utilization of grape and olive by-products as additives in animal feed. These additives have high concentration of polyphenols normally and therefore a high antioxidant capacity. The materials of the patent in question are not related to the reclaim of emulsifiers, and are different from the subject materials of the present Invention.

| Pat. No. | Patent name | Filing date | Publication date | Overview of differences from the present claims |
|---|---|---|---|---|
| US8512771B2 | Method of preparing a muscadine pomace extract | Jul. 31, 2009 | Aug. 20, 2013 | Different process of isolation; different materials claimed. |
| US6544581B1 | Process for extraction, purification and enrichment of polyphenolic substances from whole grapes, grape seeds and grape pomace | Jun. 22, 2000 | Apr. 8, 2003 | Different process of isolation; different materials claimed. |
| US8252347B1 | Stabilizing and antioxidant composition containing saw palmetto berry component and method of use | Nov. 30, 2006 | Aug. 28, 2012 | Related to saw palmetto products. |

-continued

| Pat. No. | Patent name | Filing date | Publication date | Overview of differences from the present claims |
|---|---|---|---|---|
| WO2014018922A1 | Emulsifying agent for use in food compositions | Jul. 26, 2013 | Jan. 30, 2014 | Related to soy products. |
| WO2006111163A1 | Plant extraction process | Feb. 13, 2006 | Oct. 26, 2006 | Different process of isolation; different materials claimed. |
| WO2010070836A1 | Soft drink, grape pericarp extract and methods for producing same | Dec. 4, 2009 | Jun. 24, 2010 | Technology and end product different from the ones described here. |
| US4265925 | Bland vegetable protein product and method of manufacture | Dec. 26, 1978 | May 5, 1981 | Technology and end product different from the ones described here. |
| US6238673B1 | Method of producing high flavonol content polyphenol compositions | May 14, 1999 | May 29, 2001 | Different process of isolation; different materials claimed. |
| WO2009019088A1 | Natural stabiliser system for frozen dessert | Jul. 3, 2008 | Feb. 12, 2009 | Different process of isolation; different end product. |
| WO2000072953A2 | A method of producing organic emulsifiers and organic surfactants, products produced by said method, and the use of such products | May 30, 2000 | Dec. 7, 2000 | Different process of isolation; different materials claimed. |
| US20070122505 | Natural antioxidant additive for feed and drinking water | Nov. 28, 2005 | May 31, 2007 | Different process of isolation; different materials claimed. |

STATEMENT OF FEDERALLY SPONSORED RESEARCH OR DEVELOPMENT

This Invention has been supported through the co-Financed by the European Union and the Greek State Program EPAN-II (OPC-II)/ESPA (NSRF), SYNERGASIA 2011, project code 11SYN-1701-2.

BACKGROUND OF THE INVENTION

In food, cosmetics and pharmaceutical industries there is a major need for low-cost, natural emulsifiers/stabilizers.

Million tons of grape pomace (skins, seeds and stalks) are being produced every year by the wine industry. Only in the countries of the European Union the annual production exceeds 40 million tons (Bettini, 2014). That leads to massive amounts of grape wastes, which, if not directly disposed of, they are typically being used for the production of animal feed or of compost. Until today, the best effort for the utilization of grape by-products is the reclaim of polyphenols, whose benefits in human health are widely documented (Shrikhande, 2000; Ruberto et al., 2007). The point of interest turns to the possibility of recovering food-grade materials of high added value such as emulsifying and stabilizing agents from the solid grape waste.

During processing of grape, including but not limited to the process of vinification, the cell walls of the grape rupture. These walls are reported to contain, among other substances, tannins, proteins, cellulose, and water-soluble polysaccharides (Varandas et al., 2004, Mendes, Prozil, Evtuguin & Lopes, 2013). A number of studies have reported that the water-soluble polysaccharides comprise of various monosaccharides, like arabinose, fucose, galactose, glucose, mannose, rhamnose, xylose and uronic acids (Vidal, Williams, O'Neill & Pellerin, 2001; Doco, Williams, Pauly, O'Neill & Pellerin, 2003; Prozil, Evtuguin & Lopes, 2012; Mendes et al. 2013; Rondeau, Gambier, Jolibert & Brosse, 2013). The above materials that can be retrieved from grape by-products seems appropriate for use as food-grade hydrocolloids for applications such as emulsifiers or stabilizers of food products.

REFERENCES

Bettini, O. (2014). Wine Annual Report and Statistics 2014. *USDA Foreign Agricultural Service*. Retrieved from http://gainfas.usda.gov/Recent%20GAIN%20Publications/Wine%20Annual_Rome_EU-28_2-26-2014.pdf Doco, T., Williams, P., Pauly, M., O'Neill, M. A. and Pellerin, P. (2003). Polysaccharides from grape berry cell walls. Part II. Structural characterization of the xyloglucan polysaccharides. *Carbohydrate Polymers*, 53(3), 253-261

Mendes, J. A. S., Prozil, S. O., Evtuguin, D. V. and Lopes, L. P. C. (2013). Towards comprehensive utilization of winemaking residues: Characterization of grape skins from red grape pomaces of variety Touriga Nacional. *Industrial Crops and Products*, 43(1), 25-32.

Prozil, S. O., Evtuguin, D. V. and Lopes, L. P. C. (2012). Chemical composition of grape stalks of *Vitis vinifera* L. from red grape pomaces. *Industrial Crops and Products*, 35(1), 178-184.

Rondeau, P., Gambier, F., Jolibert, F. and Brosse, N. (2013). Compositions and chemical variability of grape pomaces from French vineyard. *Industrial Crops and Products*, 43(1), 251-254.

Ruberto, G., Renda, A., Daquino, C., Amico, V., Spatafora, C., Tringali, C., & Tommasi, N. D. (2007). Polyphenol constituents and antioxidant activity of grape pomace extracts from five Sicilian red grape cultivars. *Food Chemistry*, 100(1), 203-210.

Shrikhande, A. J. (2000). Wine by-products with health benefits. *Food Research International*, 33(6), 469-474.

Varandas, S., Teixeira, M. J., Marques, J. C., Aguiar, A., Alves, A. and Bastos, M. M. S. M. (2004). Glucose and fructose levels on grape skin: Interference in *Lobesia botrana* behaviour. *Analytica Chimica Acta*, 513, 351-355.

Vidal, S., Williams, P., O'Neill, M. A. and Pellerin, P. (2001). Polysaccharides from grape berry cell walls. Part I: Tissue distribution and structural characterization of the pectic polysaccharides. *Carbohydrate Polymers*, 45(4), 315-323.

BRIEF SUMMARY OF THE INVENTION

This Invention includes: (i) a process to isolate a material from solid grape-processing waste; (ii) the said material, which is able to act as an emulsifier for the formulation of oil-in-water emulsions.

DESCRIPTION OF THE INVENTION

This Invention includes: (i) a process to isolate a material from solid grape-processing waste; (ii) the said material, which is able to act as an emulsifier for the formulation of oil-in-water emulsions.

The process for the manufacture of the material in question is as follows:

Starting material of the present invention is the solid waste obtained after any gape-processing technique, including but not limited to vinification process, henceforth called grape pomace, also referred in various sources as grape marc. This material is subjected to blanching process. During this process the grape pomace is inserted into blanching apparatus, such as a screw-blancher, for zero to tens of minutes, where it is contacted with hot steam. This process is performed in order to denature enzymes that are present to pomace, aiming at increasing the yield of the end product. The material can also be subjected to moisture reduction. Moisture reduction of grape pomace can be achieved via a number of treatments, including but not limited to drying under atmospheric pressure; drying under vacuum; freeze drying; combinations of the above.

Extraction of the exhausted grape-processing waste using ethanol-water mixtures, of a composition ranging from 50% to 98% ethanol. Extraction takes place at temperatures below 70° C. After each extraction process, the solids are separated from the liquid. This can be achieved by a number of processes, including but not limited to filtration; centrifugation; sedimentation; or combinations of the above. This extraction process under ethanol may be repeated from one to nine times, and can be seen as the relevant recycling arrow in FIG. 1 (Drawing). The resulting solid residue is of interest to this process. Residual oil can be conditionally extracted by an appropriate process, including but not limited to Soxhlet extraction. This solid product is to be called exhausted grape waste.

The material of the above treatment is subjected to aqueous extraction. The aqueous extraction solvents used in this process may nonexclusively comprise of potable water; distilled water; de-ionized water; ultra-pure water; doubly or multiply distilled or de-ionized water; or combinations of the above. The pH of the aqueous solvent may be adjusted by the use of buffer solutions of indicative but not limiting concentrations ranging from 0 to 100 mM. These buffer solutions include but are not limited to acetate and phosphate salts. The pH range of the extraction ranges between pH 3 and pH 10. Extraction temperatures can range between 50° C. and 90° C. This extraction step is to be followed by separation of the solid residues from the liquid medium. This can be achieved by a number of processes, including but not limited to filtration; centrifugation; sedimentation; reverse osmosis; microfiltration; nanofiltration; dialysis; or combinations of the above. This extraction process may be repeated from one to five times, and can be seen as the relevant recycling arrow in FIG. 1 (Drawing). The material of interest to this Invention resides in the liquid phase.

The liquid phase produced by the previous stage undergoes processing as to reduce its water content to the desired level. Moisture reduction can be achieved via a number of treatments, including, but not being limited to, drying under atmospheric pressure; rotary evaporation; drying under vacuum; freeze drying; spray drying; reverse osmosis; microfiltration; nanofiltration; dialysis; or combinations of the above. The final material (Grape Waste Emulsifier, GWE) is able to act as emulsifier and/or stabilizer for the production of dispersions such as oil-in-water emulsions. In its dry form, the material resulting from this process is a brittle, fabric-like sticky mass, typically odorless, almost tasteless, and purplish to brownish in color, its overall image depending upon a number of factors including but not limited to grape cultivar; grape age; extraction parameters. The overall process is depicted in the Drawing (FIG. 1).

The material produced by means of the process described above (GWE) is able to act as an emulsifier for the formulation and stabilization of fine dispersions of an oil into an aqueous phase, that is oil-in-water emulsions. That is, upon its dispersion or dissolution in an aqueous solution of an appropriate concentration, pH, temperature and salt content, and upon the subsequent addition of an appropriate amount of a hydrophobic liquid, including but not limited to vegetable oil, olive oil, melted fat, paraffin or hydrocarbon, or combinations of the above, and upon the enforcement of shear fields able to disrupt the oil into small droplets, the material of interest to this Invention can conditionally contribute in providing stability against flocculation, aggregation, coalescence, phase inversion, Ostwald ripening, combinations of the above, or similar destabilization mechanisms.

The stability incurred by the application of GWE manifests as a stable distribution of the droplet sizes or a small increase of the average size of the droplets for a minimum of 24 hours, as compared to the absence of an emulsifier, and within the statistical error of the method used for droplet size measurement. Typical applications include, but are not limited to: 1% w/v of the extract concentration to emulsify an oil-in-water emulsion of oil phase volume fraction of 0.1, in order to produce droplets which can remain relatively stable for a period of at least 1 day.

This invention is effective at low concentrations as an emulsifier at pH values lying between pH 2 and pH 10. The exact range of effectiveness can be narrower or wider than this range, depending on a number of factors such as the cultivar, the condition and composition of the grape waste, and the choice of extraction media and process conditions. This product can conditionally be used as an emulsifier or stabilizer in cosmetic, neutraceutical, pharmaceutical and food products. Under the above, potential applications may include but are not limited to, soups, day creams, desserts, spreads, beverages, dairy products, processed meat products, cured meat products, mayonnaise-type products, salad sauces, dressings, condiments, nutritional supplements, cocoa products, spreads, hand creams, body creams, day creams, night creams, emollient lotions, shampoos, bath formulations, drugs and relevant products.

BRIEF DESCRIPTION OF THE SEVERAL VIEWS OF THE DRAWINGS

A brief description of the Drawings presented as FIG. 1 is as follows: The solid waste is blanched; then undergoes alcohol/water extractions, the residue is separated; oil is removed from the residue; the residue undergoes aqueous extractions; the liquid is separated and then concentrated.

We claim:

1. A process for isolating biopolymer-rich extracts from grape pomace, which comprises said steps:
   (a) grape pomace is subjected to a steam blanching process, from 0 minutes to 1 hour at 70-90° C., resulting in a blanched material,
   (b) subjecting said blanched material to extraction by water-ethanol mixtures of an ethanol concentration of 50% to 98% w/w, at temperatures below 70° C., to obtain a dispersed solid,
   (c) removing the liquid from said dispersed solid as to obtain a solid residue,
   (d) treating said solid residue with an organic solvent at temperatures from 20° C. to 90° C. and for times from ten minutes and twenty-four hours as to obtain a defatted solid material,
   (e) extracting said defatted solid material by an aqueous solvent, at temperatures from 20° C. to 90° C. and for times from ten minutes to twenty-four hours, as to obtain a biopolymer-rich liquid extract.

2. A biopolymer-rich solid extract obtained by drying the biopolymer-rich liquid extract of claim 1.

3. A food product comprising the biopolymer-rich liquid extract of claim 1.

4. An emulsion product comprising the biopolymer-rich liquid extract of claim 1.

5. A cosmetic product comprising the biopolymer-rich liquid extract of claim 1.

6. A food ingredient comprising the biopolymer-rich solid extract of claim 2.

7. A food product comprising the biopolymer-rich solid extract of claim 2.

8. An emulsion product comprising the biopolymer-rich solid extract of claim 2.

9. A cosmetic product comprising the biopolymer-rich solid extract of claim 2.

* * * * *